(12) United States Patent
Drake et al.

(10) Patent No.: US 8,735,756 B1
(45) Date of Patent: *May 27, 2014

(54) SYSTEM AND METHOD FOR PROCESSING MAIL

(75) Inventors: Paul E. Drake, San Antonio, TX (US); John R. Krause, Fair Oaks Ranch, TX (US); George R. Nortzon, Boerne, TX (US); Val L. Windham, San Antonio, TX (US); John P. Baeseman, Columbus, WI (US); Tonya R. Lozano, Helotes, TX (US); Henry E. Austin, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 203 days.

This patent is subject to a terminal disclaimer.

(21) Appl. No.: 12/947,581

(22) Filed: Nov. 16, 2010

Related U.S. Application Data

(63) Continuation of application No. 11/565,705, filed on Dec. 1, 2006, now Pat. No. 7,834,288, which is a continuation of application No. 10/981,819, filed on Nov. 5, 2004, now Pat. No. 7,170,023.

(60) Provisional application No. 60/517,810, filed on Nov. 6, 2003.

(51) Int. Cl.
*B07C 5/00* (2006.01)

(52) U.S. Cl.
USPC .......................................... 209/583; 422/117

(58) Field of Classification Search
USPC ......... 209/577, 579, 583, 589, 656, 657, 900, 209/937; 422/117, 946; 454/255
See application file for complete search history.

(56) References Cited

U.S. PATENT DOCUMENTS

| | | | |
|---|---|---|---|
| 4,304,224 A | 12/1981 | Fortney | |
| 5,099,751 A * | 3/1992 | Newman et al. | 454/238 |
| 5,626,820 A | 5/1997 | Kinkead et al. | |
| 6,387,332 B1 | 5/2002 | Dickinson et al. | |
| 6,551,182 B2 * | 4/2003 | Caracciolo, Jr. | 452/81 |
| 6,692,696 B1 | 2/2004 | Alberte | |

(Continued)

OTHER PUBLICATIONS

U.S. Appl. No. 60/337,674, Call, et al. filed Nov. 13, 2001. 108 pgs.

*Primary Examiner* — Joseph C Rodriguez

(74) *Attorney, Agent, or Firm* — Baker and Hostetler LLP

(57) ABSTRACT

A threat detection system includes a facility including at least three separate rooms located in the facility and a positive pressure zone located external to the facility. A ventilation system is coupled to the at least three separate rooms. A first room is located in the facility, wherein the first room includes a first room pressure zone that is negative with respect to the positive pressure zone external to the facility. A second room is located in the facility and connected to the first room, wherein the second room includes a second room pressure zone that is negative with respect to the first room pressure zone. A third room is located in the facility and connected to the second room, wherein the third room includes a third room pressure zone that is negative with respect to the positive pressure zone external to the facility and positive with respect to the second room pressure zone, whereby the first room pressure zone, the second room pressure zone, and the third room pressure zone result in air within the facility or entering the facility to flow into the second room.

9 Claims, 7 Drawing Sheets

(56) References Cited

U.S. PATENT DOCUMENTS

| | | |
|---|---|---|
| 6,697,500 B2 | 2/2004 | Woolston et al. |
| 6,740,836 B2 | 5/2004 | Ryan et al. |
| 6,887,710 B2 | 5/2005 | Call et al. |
| 6,960,244 B2 | 11/2005 | Lehman |
| 7,024,019 B2 | 4/2006 | Sansone |
| 7,170,023 B1 | 1/2007 | Drake et al. |
| 7,265,253 B2 | 9/2007 | Mielnik et al. |
| 7,707,931 B2 | 5/2010 | Garrett et al. |
| 7,834,288 B1 * | 11/2010 | Drake et al. .......... 209/583 |
| 2003/0047087 A1 * | 3/2003 | Phebus et al. .......... 99/516 |
| 2003/0115931 A1 | 6/2003 | Stemmle et al. |
| 2004/0028561 A1 | 2/2004 | Daugherty et al. |
| 2004/0029521 A1 | 2/2004 | Cauthorne |

* cited by examiner

SYSTEM AND METHOD FOR PROCESSING MAIL

CROSS REFERENCE TO RELATED APPLICATIONS

The present application is a Continuation of U.S. application Ser. No. 11/565,705, filed on Dec. 1, 2006, which is a Continuation of U.S. application Ser. No. 10/981,819, filed on Nov. 5, 2004, now U.S. Pat. No. 7,170,023, which claims priority to U.S. Application Ser. No. 60/517,810 filed on Nov. 6, 2003, the disclosures of which are incorporated herein by reference.

BACKGROUND

The disclosures herein relate generally to a mail processing system and more particularly to processing mail with a threat detection and response system.

Mail service providers, such as the United States Postal Service, may handle hundreds of billions of letters and parcels each year. Mail is received from domestic and international sources every day. The receipt and processing of mail involves considerable handling and movement of that mail in order to sort and deliver it to its intended recipient.

A number of machines may be used to manipulate the mail in order to move it through the processing system. Mail joggers may be used to vibrate the mail prior to opening it to get the contents to one side. Mail cutting machines may be used to slice envelopes open. Machines, such as a mail sorting machine, may be used to cut and sort the mail. Machines, such as an OPEX 150 machine, may be used to open mail containing checks and receipts, and extract the check and receipt from the envelope. Machines, such as an OPEX 50 and 51 machine, may be used to provide an assist function for hand extraction and inspection of mail. Mailroom workers may be used to open and inspect mail by hand. Packages may move along a conveying system to be inspected by machine or mailroom workers.

In recent years, a new issue has arisen involving the handling of mail. Mail containing agents, such as anthrax or ricin, have been sent through the postal system. However, because of the systems set up to process and deliver the mail, the letter's recipient is not the only person subject to exposure. Due to the handling and movement this mail experiences during processing, the agents in that mail may escape sometime during the process, and other pieces of mail may be contaminated. Furthermore, detection of these agents usually results from the opening of the mail containing them, subjecting workers in mail processing facilities to exposure. Once the agents escape from the contaminated mail, the contamination of neighboring areas arises, possibly through the air or from transport by a contaminated worker.

Accordingly, it would be desirable to provide an improved mail processing system absent the disadvantages found in the prior methods discussed above.

SUMMARY

One embodiment, accordingly, provides a threat detection system including a facility comprising at least three separate rooms located in the facility and a positive pressure zone located external to the facility, a ventilation system coupled to the at least three separate rooms, a first room located in the facility, wherein the first room comprises a first room pressure zone that is negative with respect to the positive pressure zone external to the facility, a second room located in the facility and connected to the first room, wherein the second room comprises a second room pressure zone that is negative with respect to the first room pressure zone, and a third room located in the facility and connected to the second room, wherein the third room comprises a third room pressure zone that is negative with respect to the positive pressure zone external to the facility and positive with respect to the second room pressure zone, whereby the first room pressure zone, the second room pressure zone, and the third room pressure zone result in air within the facility or entering the facility to flow into the second room.

A principal advantage of this embodiment is that incoming mail to a facility may be sorted and inspected while limiting the risks to the workers and the facility where the mail is processed.

DETAILED DESCRIPTION

Figure 1:
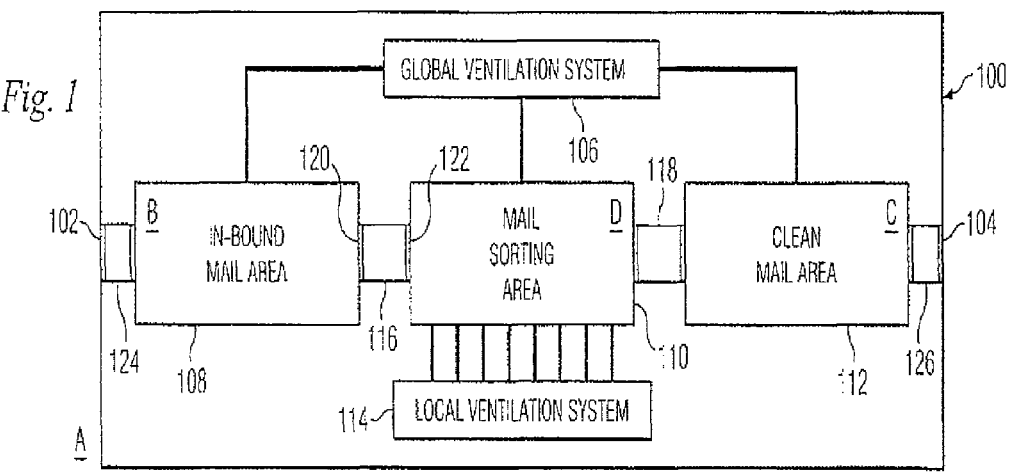
FIG. 1 is a schematic view illustrating an embodiment of a system for mail processing with threat detection and worker protection.

In one embodiment, a system and method for mail processing includes an environmentally isolated mail processing facility 100, FIG. 1. Facility 100 achieves environmental isolation through a variety of means, discussed below, that result in the air circulating through the facility 100 being contained to the facility 100 and not escaping to neighboring facilities (not shown). Facility 100 includes a plurality of facility access doors 102 and 104 which may provide a connection to other facilities (not shown) adjacent to the facility 100, or may provide an exit from the facility 100 to the outdoors. A global ventilation system 106 is used to ventilate areas within facility 100. Global ventilation system 106 helps to achieve environmental isolation of facility 100 by being dedicated to facility 100 and not connected to other facilities. Thus, air existing in facility 100 may circulate through the facility or exit to the outdoors, but is limited from entering neighboring facilities through the global ventilation system 106. Global ventilation system 106 may include a high efficiency particulate arresting (HEPA) filter to sanitize air recirculated through the facility 100. A plurality of areas exist within the facility 100, including in-bound mail area 108, mail sorting area 110, and clean mail area 112, with each area 108-112 coupled to the global ventilation system 106. In-bound mail area 108 includes facilities for receiving mail from outside sources and preparing the mail to be sorted. Mail sorting area 110 includes a plurality of devices for processing and sorting the mail, each of which may be coupled to a local ventilation system 114. Local ventilation system 114 is provided for circulating air through the devices and detecting mails threats in mail processed and sorted by the devices and is discussed in more detail below. Clean mail area 112 includes facilities for storing and moving mail that has been processed and sorted in the mail sorting area 110 in preparation for delivering the mail to its recipient.

A system and method for mail processing may process mail in batches. For example, all mail entering in-bound mail area 108 together will be grouped into batches and processed together through the other areas 110 and 112 of facility 100. A given batch must exit together, so no mail will leave the mail sorting area 110 until all the mail in the batch it entered with is processed and ready to leave. Batch processing provides that if a mail threat is detected, it will be limited to the area the batch is being processed in, and not spread throughout the facility or other facilities due to a cross contaminated piece of mail leaving the area ahead of the batch it entered with.

Environmentally isolated mail processing facility 100 is surrounded by an area A which is at a positive pressure. A plurality of areas B, C, and D exist within the facility 100 which are all kept at a negative pressure with respect to area A. Area B may exist within the inbound mail area 108. Area C may exist within the clean mail area 112. Area D may exist within the mail sorting area 110. In one embodiment, areas B, C, and D may all be of the same pressure. The pressure differential between area A and areas B, C, and D help to environmentally isolate facility 100 by providing that air circulating within facility 100 will not escape facility 100. When an area in the facility 100 is opened to area A, air will flow from the region of positive pressure to regions of negative pressure, providing that air circulating within the facility 100 will stay within the facility 100, and mail threats discovered within the facility 100 which may have become airborne will be limited from escaping from the facility. In another embodiment, area D may be of a negative pressure with respect to areas B and C, both of which are of a negative pressure with respect to area A, resulting in airflow through the facility being directed toward area D. Area D may then be situated in an area where the highest number of mail threats are expected to be discovered, such as the mail sorting area 110, to provide that air from the mail sorting area 110 is limited from escaping to other areas of the facility 100.

Areas 108-112 within facility 100 may exist in the same room, or may be coupled to each other through access areas such as access areas 116 and 118. Access area 116 may include interlocking doors 120 and 122 which operate together such that only one may be opened at a time. For example, in order to move from in-bound mail area 108 to mail sorting area 110, interlocking door 120 must be opened. However, interlocking door 120 cannot be opened unless interlocking door 122 is closed. Once interlocking door 120 is opened, it must be closed in order to open interlocking door 122 and enter mail sorting area 110. Interlocking doors, such as interlocking doors 120 and 122, may also exist in access area 11B, and in facility access areas 124 and 126.

Environmentally isolated mail processing facility 100 will also include a mail threat response system which will be able to seal the access doors 102 and 104 of facility 100 if they provide access to other facilities (not shown). Facility access doors that provide access to the outdoors will not be sealed. Sealing the facility 100 in this manner provides that a discovered mail threat will be limited from spreading to attached facilities, but will still allow mail workers to leave the facility when a mail threat is detected limiting the risk of contaminating others.

Figure 2:
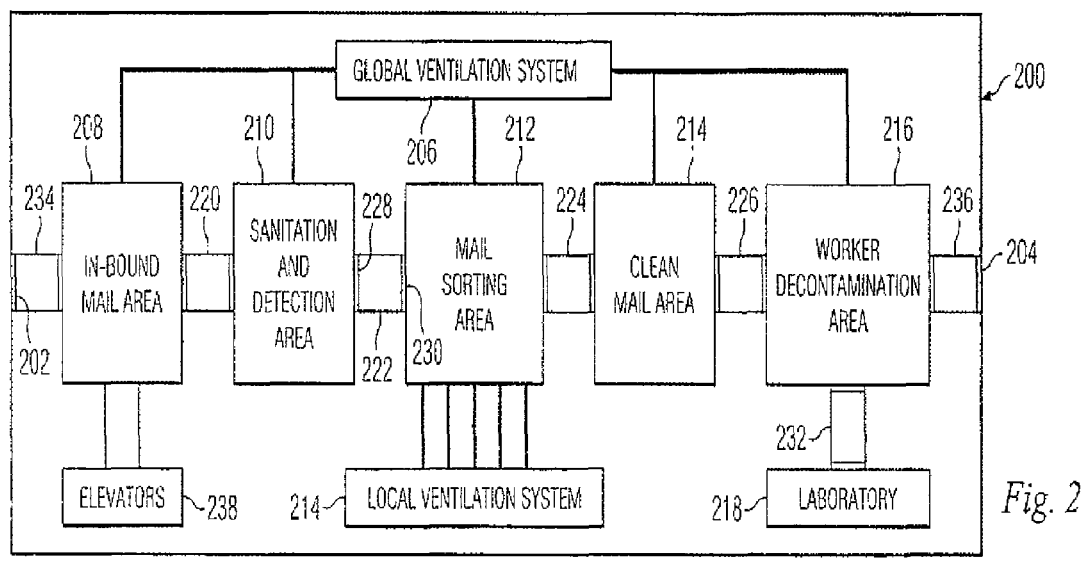
FIG. 2 is a schematic view illustrating another embodiment of a system for mail processing with threat detection and worker protection.
Figure 3:
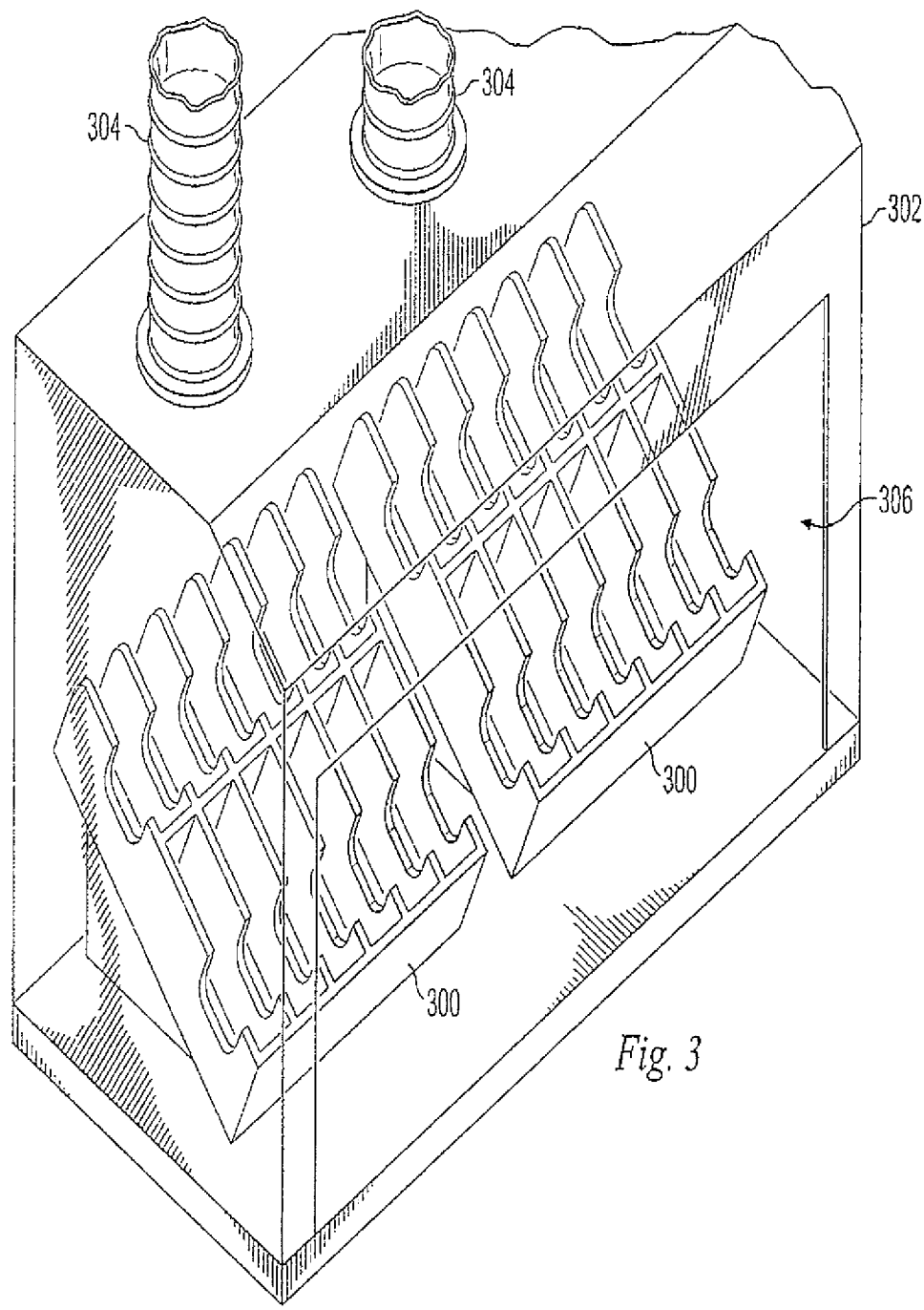
FIG. 3 is perspective view illustrating an embodiment of a mail jogger machine coupled to a local ventilation system.

In one embodiment, a system and method for mail processing includes an environmentally isolated mail processing facility 200, FIG. 2. Facility 200 achieves environmental isolation through a variety of means, discussed below, that provide for the air circulating through the facility 200 being contained to the facility 200 and limited from escaping to neighboring facilities (not shown). Facility 200 includes a plurality of facility access doors 202 and 204 which may provide a connection to other facilities (not shown) adjacent to the facility 200, or may provide an exit from the facility 200 to the outdoors. A global ventilation system 206 is used to ventilate areas within facility 200. Global ventilation system 206 helps to provide for environmental isolation of facility 200 by being limited to facility 200 and not connected to other facilities. Thus, air existing in facility 200 may circulate through the facility or exit to the outdoors, but is limited from entering neighboring facilities through the global ventilation system 206. Global ventilation system 206 may include a HEPA filter to sanitize air recirculated through the facility 200. A plurality of areas exist within the facility 200, including in-bound mail area 208, sanitation and detection area 210, mail sorting area 212, clean mail area 214, worker decontamination area 216, and laboratory 218, with each area 208-218 coupled to the global ventilation system 206. In-bound mail area 208 includes facilities for receiving mail from outside sources and preparing the mail to be sorted. In bound mail area 208 may also include a detector for detecting ionizing radiation in inbound mail. Sanitation and detection area 210 includes systems for sanitizing mail that may contain a threat, such as electron beam systems provided to neutralize biological agents, and systems for detecting threats within the maU, such as imaging systems provided to detect radioactive material, explosives, and other devices. Mail sorting area 212 includes a plurality of devices for processing and sorting the mail, each of which may be coupled to a local ventilation system 214. Local ventilation system 214 is dedicated to ventilating air circulated through the devices and detecting mail threats in mail processed and sorted by the devices and is discussed in more detail below. Clean mail area 214 includes facilities for storing and moving mail that has been processed and sorted in the mail sorting area 212 in preparation for delivering the mail to its recipient. Worker decontamination area 216 includes decontamination equipment such as showers and eyewashes for workers who may have been exposed to a mail threat. Worker decontamination area may be situated next to a facility access door that exits to the outdoors so that workers who have been decontaminated may exit facility 200 without having to encounter an area that has been potentially contaminated. Laboratory 218 includes equipment for analyzing a detected mail threat to determine various information such as what type of threat has been detected.

Areas 208-218 within facility 200 may exist in the same room, or may be coupled to each other through access areas such as access areas 220, 222, 224, and 226. Access area 222 may include interlocking doors 228 and 230 which operate together such that only one may be opened at a time. For example, in order to move from in-bound mail area sanitation and detection area 210 to mail sorting area 212, interlocking door 228 must be opened. However, interlocking door 228 cannot be opened unless interlocking door 230 is closed.

Once interlocking door 228 is opened, it must be closed in order to open interlocking door 230 and enter mail sorting area 212. Interlocking doors, such as interlocking doors 228 and 230, may exist in access area 220, 224, and 226, laboratory access area 232, and facility access areas 234 and 236.

Environmentally isolated mail processing facility 200 will also include a mail threat response system which will be able to seal the access doors 202 and 204 of facility 200 if they provide access to other facilities (not shown). Facility access doors that provide access to the outdoors will not be sealed. Sealing the facility 200 in this manner provides that a discovered mail threat is limited from spreading to attached facilities, but will still allow mail workers to leave the facility when a mail threat is detected and limiting risk of contaminating others. Facility 200 may also include an elevator 238. Elevator 238 may be a single elevator or a plurality of elevators, and the mail threat response system will be able to deactivate the elevator 238 in the event a mail threat is detected in order to prevent access to facility 200.

Environmentally isolated mail processing facility 200 also includes the pressure differentials inside and outside the facility 200 similar to those described for facility 100 of FIG. 1 such that when a facility access door 202 or 204 is opened, air will flow from outside the facility 200 to within the facility, provided to keep the facility 200 environmentally isolated from neighboring facilities (not shown). Areas 208, 210, 212, 214, and 216 may also vary in pressure such that air flows within the facility to the area most likely to discover a mail threat, such as mail sorting area 212, provided to keep mail threats which are discovered limited to that area. Batch processing of mail, described above, may also be used within facility 200.

Referring to FIG. 3-9, the mail processing area and local ventilation system such as those described in FIGS. 1 and 2 will now be described in more detail. The plurality of devices for processing and sorting the mail in the mail processing area includes a mail jogger machine 300, FIG. 3. Mail jogger 300 is used to vibrate the mail prior to machine manipulation and opening to get the contents of the mail to one side. This process has the potential to release any particulate matter included with the mail. A jogger hood 302 is employed to contain particulate matter that might be released during operation of the jogger 300. Jogger hood 300 may be made of a clear material to the viewing of mail in the jogger machine while being physically separated from the mail. Local ventilation connectors 304 couple the jogger 300 to the local ventilation system (not shown). Jogger hood 302 includes an opening 306 to allow access to the mail in the jogger 300. Local ventilation system draws air through the opening 306 at a rate sufficient to substantially provide that particulate matter released from the mail will flow into the local ventilation connectors 304 and through local ventilation system and not out through opening 306.

Figure 4:
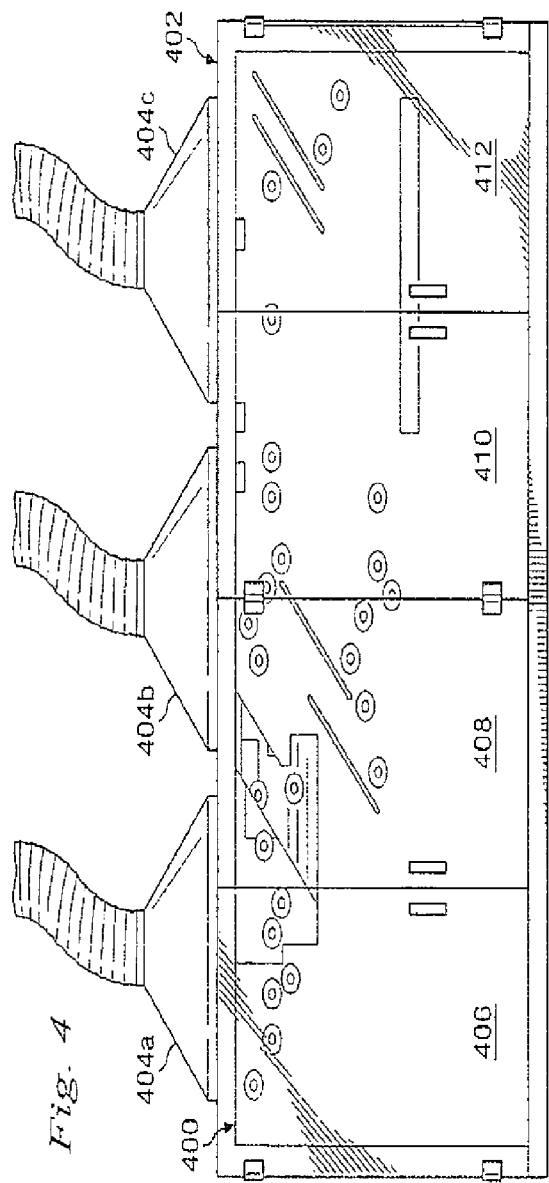
FIG. 4 is a perspective view illustrating an embodiment of a check and receipt opening machine coupled to a local ventilation system.

The plurality of devices for processing and sorting the mail in the mail processing area also includes an check and receipt opening machine 400, FIG. 4, such as an OPEX 150 machine. Machine 400 opens mail containing checks and receipts, and during the process, the check and/or receipt are extracted from the mail. This process has the potential to release any particulate matter included with the mail. The machine 400 is enclosed within a machine cover 402 to contain any particulate matter that might be released during operation of machine 400. Machine cover 400 may be made of a clear material to allow the viewing of mail in machine 400 while being physically separated from the mail. Local ventilation connectors 404a, 404b, and 404c couple the machine 400 to the local ventilation system (not shown). Machine cover 402 includes a plurality of doors 406, 408, 410, and 412 for allowing access to mail in machine 400. Local ventilation system draws air through machine 400 at a rate sufficient to substantially provide that particulate matter released from the mail will flow into the local ventilation connectors 404 and through local ventilation system.

Figure 5:
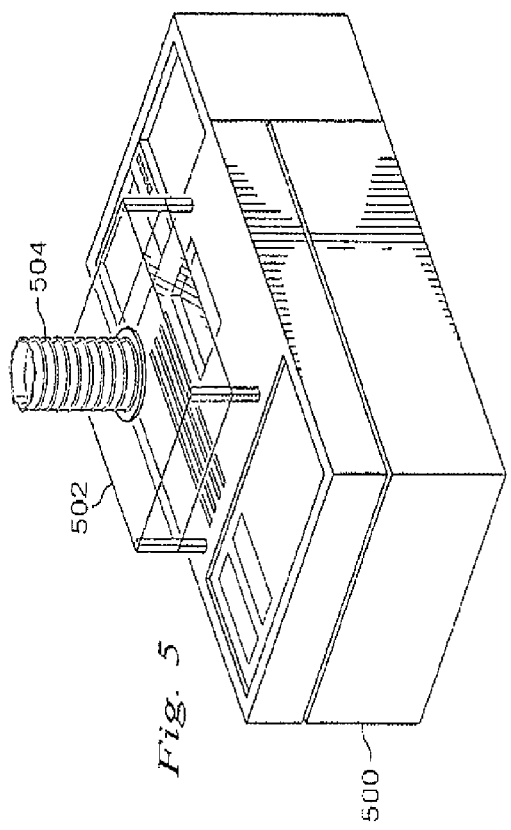
FIG. 5 is a perspective view illustrating an embodiment of a mail opening machine coupled to a local ventilation system.

The plurality of devices for processing and sorting the mail in the mail processing area also includes an mail opening machine 500, FIG. 5. Machine 500 slices open envelopes, and this process has the potential to release any particulate matter included with the mail. Machine 500 includes a hood 502 provided to capture particulate matter that might be released during operation of machine 500. Hood 502 may be made of a clear material to allow the viewing of mail in machine 500 while being physically separated from the mail. Local ventilation connector 504 couples machine 500 to local ventilation system (not shown). Local ventilation system draws air through machine 500 at a rate sufficient to substantially provide that particulate matter released from the mail will flow into the local ventilation connectors 304 and through local ventilation system.

Figure 6:
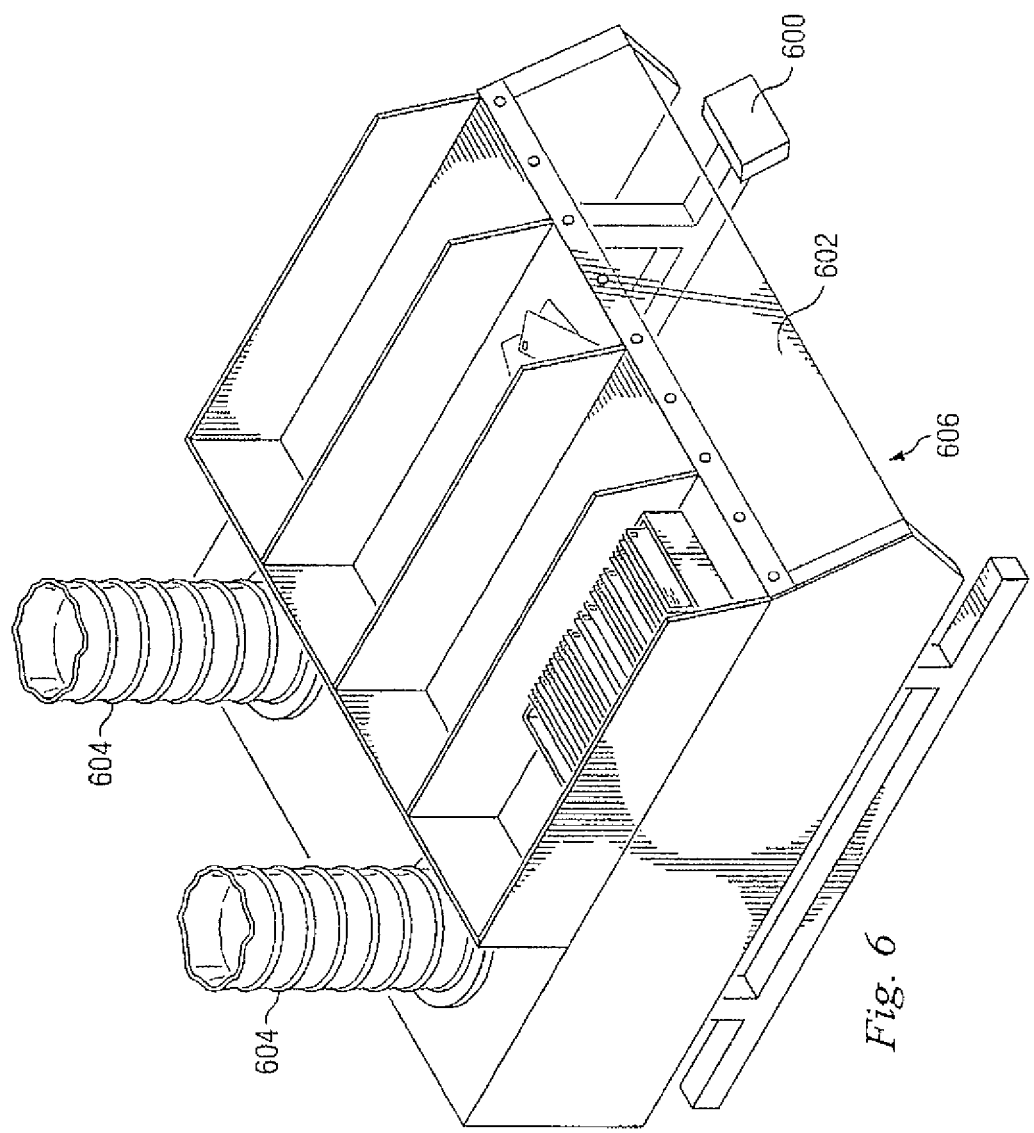
FIG. 6 is a perspective view illustrating an embodiment of a worker assist machine coupled to a local ventilation system.

The plurality of devices for processing and sorting the mail in the mail processing area also includes an worker assist machine 600, FIG. 6, such as an OPEX 50 or OPEX 51. Machine 600 provides a machine assist function for hand extraction and inspection of mail by mail workers. Machine 600 includes a hood 602 to capture particulate matter that might be released during operation of the machine 600 or hand extraction and inspection by the mail worker. Hood 602 may be made of a clear material to allow the viewing of mail in and from machine 600 while being physically separated from the mail. Local ventilation connectors 604 couple machine 600 to the local ventilation system (not shown). An opening 606 is provided to allow the mail worker to inspect mail that has been opened by the machine. Local ventilation system draws air through opening 608 at a rate sufficient to substantially provide particulate matter released from the mail to flow into the local ventilation connectors 604 and through local ventilation system.

Figure 7:
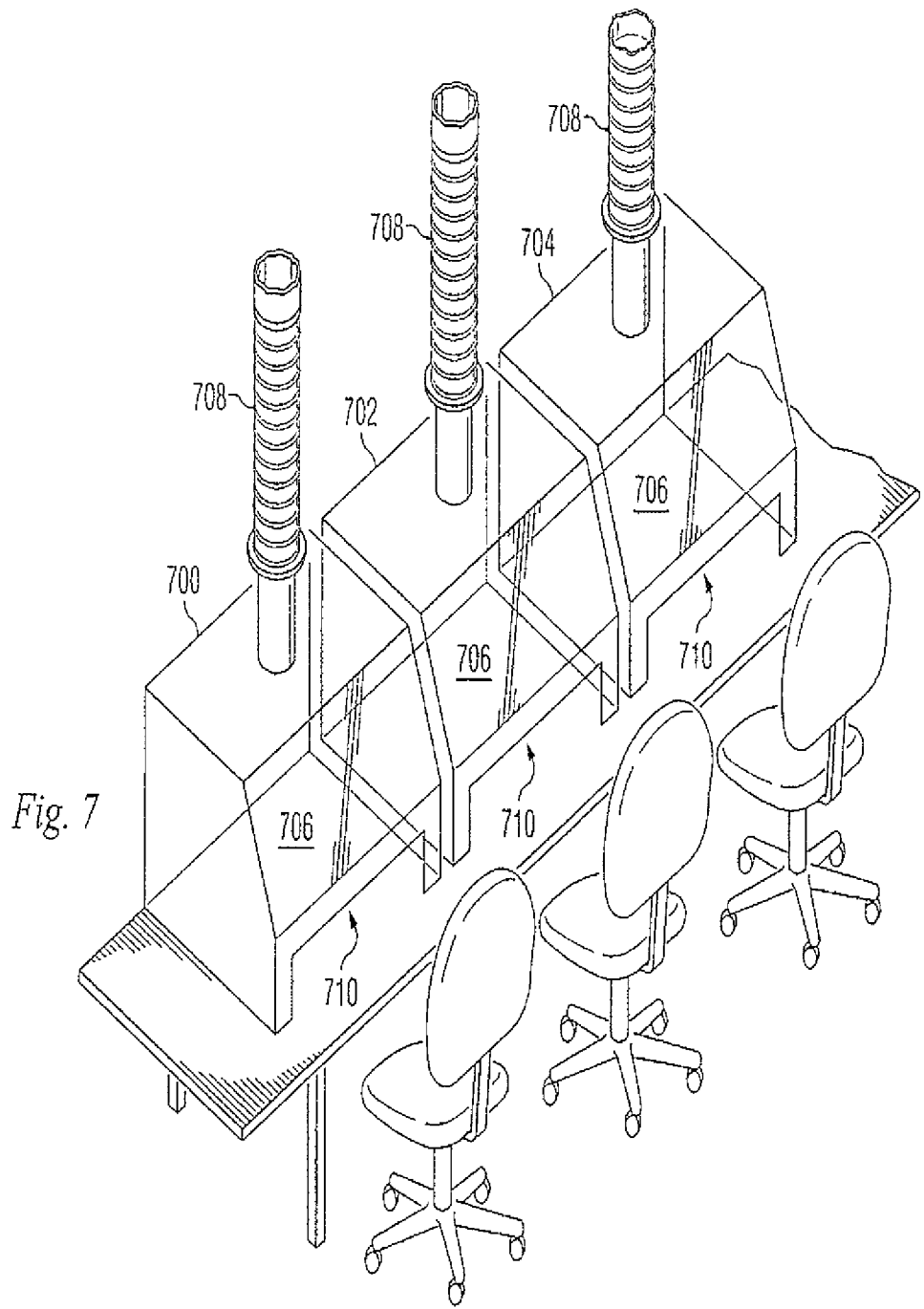
FIG. 7 is a perspective view illustrating an embodiment of a hand inspection station coupled to a local ventilation system.

The plurality of devices for processing and sorting the mail in the mail processing area also includes a plurality of hand inspection stations such as stations 700, 702, and 704, FIG. 7. Hand inspection stations 700-704 are areas where mail workers open and inspect entering mail by hand. Each station includes a hood 706 to capture particulate matter that might be released during opening and inspection of the mail. Hood 706 may be made of a clear material to allow the viewing of mail through hood 706 at hand inspection station 700-704. Local ventilation connector 708 couples hand inspection station to the local ventilation system (not shown). An opening 710 allows the mail worker to open and inspect the mail while keeping the mail within the hood 706. Local ventilation system draws air through opening 710 at a rate sufficient to substantially provide particulate matter released from the mail to flow into the local ventilation connector 708 and through local ventilation system.

Figure 8:
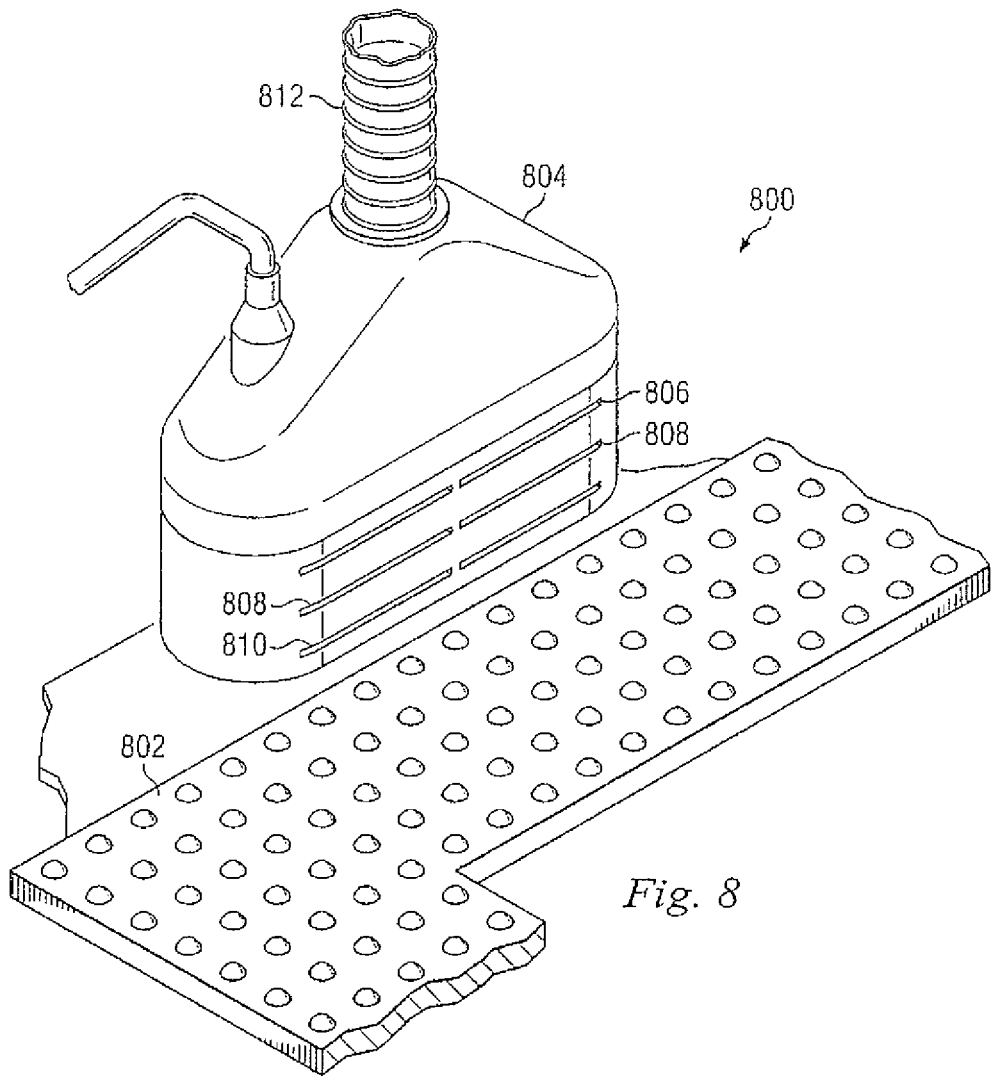
FIG. 8 is a perspective view illustrating an embodiment of a package inspection station coupled to a local ventilation system.

The plurality of devices for processing and sorting the mail in the mail processing area also includes a package inspection station 800, FIG. 8. Package inspection station 800 is for inspecting oversized mail and includes a conveying surface 802 for moving packages through the inspection station. A hood 804 is provided adjacent to the conveyor surface 802 and includes a plurality of vents 806, 808, and 810 for drawing air from packages on the conveyor surface into a local ventilation connector 812 Local ventilation system draws air through vents 806-810 at a rate sufficient to substantially provide particulate matter released from the mail to flow into the local ventilation connector 708 and through local ventilation system.

Figure 9:
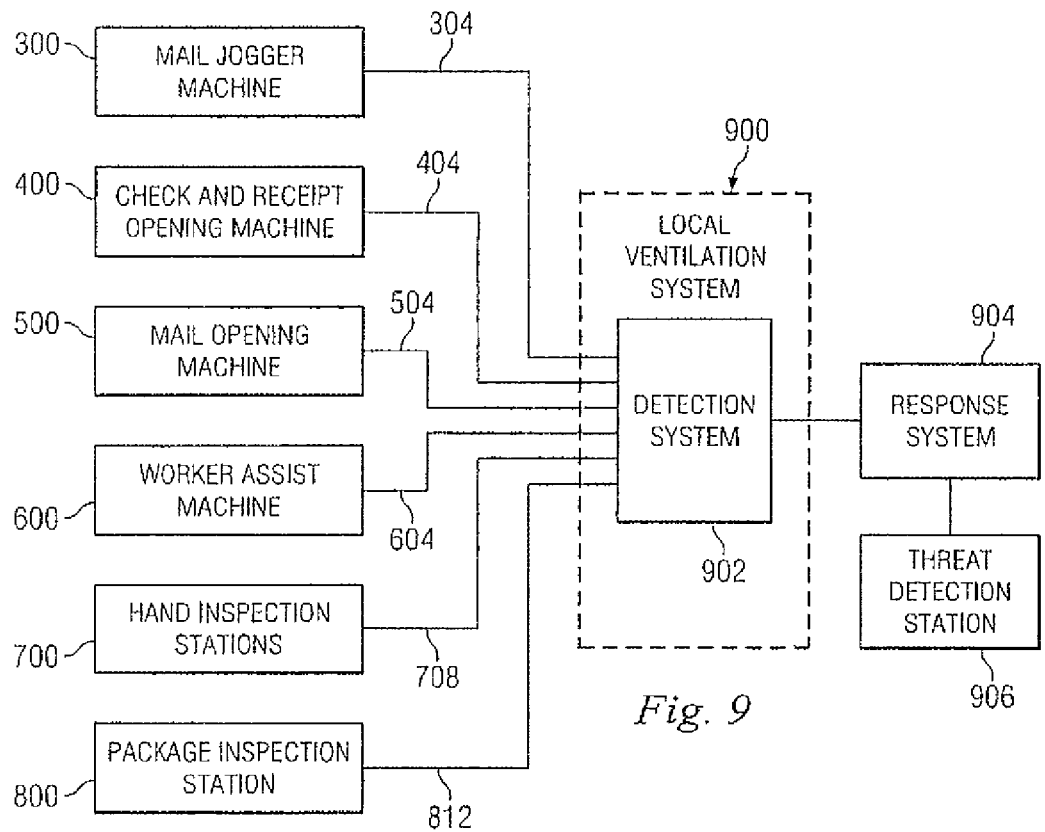
FIG. 9 is a schematic view illustrating an embodiment of a local ventilation system coupled to a response system and a plurality of devices for processing and sorting the mail.

Local ventilation system 900, FIG. 9, may be used as the local ventilation system 114 of FIG. 1 and the local ventilation system 214 of FIG. 2. Local ventilation system 900 is coupled to mail jogger machine 300, check and receipt opening machine 400, mail opening machine 500, worker assist machine 600, hand inspection stations 700, and package inspection station 800 by local ventilator connectors 304, 404, 504, 604, 708, and 812 respectively. Local ventilation system 900 draws air at a rate through local ventilator connectors 304, 404, 504, 604, 708, and 812 sufficient to substantially provide particulate matter released from mail being processed through mail processing equipment to enter the local ventilation system 900, and to provide that ducts leading to a detection system 902 remain clear. Ventilator connectors 304, 404, 504, 604, 708, and 812 are all coupled to detection system 902 that may be within the local ventilation system 900 or coupled to the local ventilation system 900. Detection system 802 monitors the air circulating through the local ventilation system 900 to detect mail threats existing in the mail being processed through machines 300, 400, 500 and 600 and stations 700 and 800. Detection system 902 may be a single system coupled to the sorting and processing equipment 300, 400, 500, 600, 700, and 800, or a plurality of detection systems, each coupled to a given piece of the equipment. Using a plurality of systems each connected to a piece of equipment enables fast location of a detected mail threat. Detection system 902 may include a laser particle counter, such as a MetOne Model 2400 Airborne Particle Counter, which detects an increase in particles in the air, or a device that can recognize biological or chemical agents which are circulating through the system. In the event the detection system 902 detects a mail threat in the local ventilation system 900, a response system 904 may be triggered.

Figure 10:
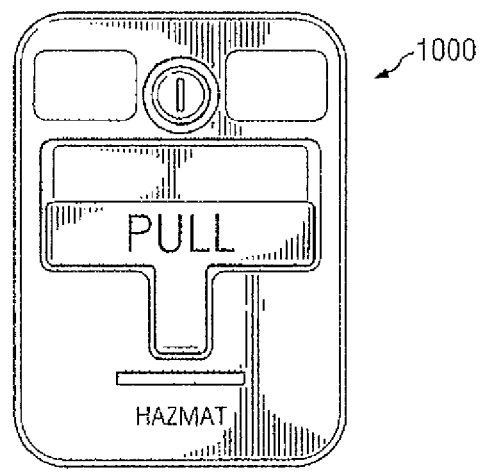
FIG. 10 is a front view illustrating an embodiment of a threat detection station.

Response system 904 may operate to seal off exits and entrances to other inhabited facilities, and deactivate elevators that might allow access to the contaminated area. Response system 904 may further sound alarms and provide instructions to mail workers on how to proceed in the event of detecting a mail threat. Response system 904 may initiate a worker decontamination procedure for workers in the event a mail threat is detected. The worker decontamination procedure may include locking down the facility, a contaminated mail hand-off procedure that documents who handled contaminated mail and where that mail has been in the facility, worker decontamination, contaminated mail analysis, and emergency response entry to decontaminate the facility. Response system 904 may also be triggered through a threat detection station 906 such as a pull station 1000, FIG. 10. Pull station 1000 may be one of a plurality of threat detection stations placed throughout environmentally isolated mail processing facility 100 or 200, FIG. 1 and FIG. 2, and may be activated by a mail worker in the event a mail threat is detected other than from the detection system through the local ventilation system.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed:

1. A threat detection system comprising:
   a facility including a mail processing room located in the facility and a positive pressure zone located external to the facility;
   a ventilation system coupled to the mail processing room;
   a first interlocking door-less area located in the mail processing room, wherein the first interlocking door-less area includes a first area pressure zone that is negative with respect to the positive pressure zone external to the facility;
   a second interlocking door-less area located in the mail processing room, wherein the second interlocking door-less area includes a second area pressure zone that is negative with respect to the first area pressure zone, wherein the ventilation system includes a local ventilation system to supply air to the second interlocking door-less area; and
   a third interlocking door-less area located in the mail processing room, wherein the third interlocking door-less area includes a third door-less area pressure zone that is negative with respect to the positive pressure zone external to the facility and positive with respect to the second area pressure zone, wherein the first area pressure zone, the second area pressure zone, and the third area pressure zone result in air within the facility or entering the facility to flow into the second area, and wherein the ventilation system includes a global ventilation system having a dedicated input to the first interlocking door-less area, a dedicated input to the second interlocking door-less area, and a dedicated input to the third interlocking door-less area.

2. The system of claim 1 wherein the global ventilation system is operable to environmentally isolate the facility.

3. The system of claim 1 wherein the first door-less area is configured for receiving a possible threat carrier.

4. The system of claim 1 wherein the second door-less area is configured for sorting and inspecting a possible threat carrier.

5. The system of claim 1 wherein the third door-less area is configured for temporarily storing a possible threat carrier that has been sorted and inspected.

6. The system of claim 1 further comprising:
   a fourth area located in the mail processing room including a sanitation module for sanitizing a possible threat carrier, wherein the fourth area includes a fourth area pressure zone that is negative with respect to the first area pressure zone and positive with respect to the second area pressure zone, whereby the first area pressure zone, the second area pressure zone, the third area pressure zone, and the fourth area pressure zone result in air within the facility or entering the facility to flow into the second area.

7. The system of claim 1 further comprising:
   a fifth area located in the mail processing room including an imaging machine for detecting hazardous material in a possible threat carrier.

8. The system of claim 1 further comprising:
   a sixth area located in the mail processing room including a worker decontamination equipment, wherein the sixth area includes a sixth area pressure zone that positive with respect to the third area pressure zone, whereby the first area pressure zone, the second area pressure zone, the third area pressure zone, and the sixth area pressure zone result in air within the facility or entering the facility to flow into the second area.

9. The system of claim 1 further comprising:
a seventh area located in the mail processing room including a threat analyzing laboratory, wherein the seventh area includes a seventh area pressure zone that is positive with respect to the third area pressure zone, whereby the first area pressure zone, the second area pressure zone, the third area pressure zone, and the seventh area pressure zone result in air within the facility or entering the facility to flow into the second area.

* * * * *

UNITED STATES PATENT AND TRADEMARK OFFICE
CERTIFICATE OF CORRECTION

PATENT NO. : 8,735,756 B1  
APPLICATION NO. : 12/947581  
DATED : May 27, 2014  
INVENTOR(S) : Paul Eugene Drake et al.

Page 1 of 1

It is certified that error appears in the above-identified patent and that said Letters Patent is hereby corrected as shown below:

On the title page item (75), Inventor's name is spelled incorrectly: George Randall should be George Randall <u>Notzon</u>

Signed and Sealed this

Ninth Day of September, 2014

Michelle K. Lee  
*Deputy Director of the United States Patent and Trademark Office*